US008816959B2

(12) United States Patent
Pan et al.

(10) Patent No.: US 8,816,959 B2
(45) Date of Patent: Aug. 26, 2014

(54) METHOD AND APPARATUS FOR OBTAINING AND/OR ANALYZING ANATOMICAL IMAGES

(75) Inventors: Lihong Pan, Brookfield, WI (US); Kirstin Nora LaConte, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 704 days.

(21) Appl. No.: 11/732,419

(22) Filed: Apr. 3, 2007

(65) Prior Publication Data

US 2008/0246724 A1 Oct. 9, 2008

(51) Int. Cl.
*G06F 3/033* (2013.01)
*G09G 5/08* (2006.01)
*A61B 8/00* (2006.01)
*G01S 7/52* (2006.01)
*G06F 19/00* (2011.01)

(52) U.S. Cl.
CPC ......... *G01S 7/52074* (2013.01); *G01S 7/52073* (2013.01); *G06F 19/321* (2013.01)
USPC ............ 345/157; 382/128; 345/158; 600/437

(58) Field of Classification Search
USPC ................. 345/1.1–1.3, 156–184; 34/157
See application file for complete search history.

(56) References Cited

U.S. PATENT DOCUMENTS

| 5,873,829 | A | 2/1999 | Kamiyama et al. |
|---|---|---|---|
| 6,996,432 | B2 | 2/2006 | Ostrovsky et al. |
| 7,044,914 | B2 | 5/2006 | Kawagishi et al. |
| 2001/0002830 | A1* | 6/2001 | Rahn et al. ................ 345/158 |
| 2003/0215119 | A1 | 11/2003 | Uppaluri et al. |
| 2003/0215120 | A1 | 11/2003 | Uppaluri et al. |
| 2005/0210444 | A1* | 9/2005 | Gibson et al. ............... 717/108 |
| 2006/0184019 | A1 | 8/2006 | Ito et al. |
| 2006/0215894 | A1 | 9/2006 | Lakare |
| 2006/0239523 | A1 | 10/2006 | Stewart et al. |
| 2006/0241431 | A1* | 10/2006 | Kamiyama .................. 600/437 |
| 2007/0003119 | A1 | 1/2007 | Roehrig et al. |
| 2007/0167758 | A1* | 7/2007 | Costello ..................... 600/437 |
| 2007/0258632 | A1* | 11/2007 | Friedman et al. ............ 382/128 |
| 2008/0044068 | A1* | 2/2008 | Evertsz et al. .............. 382/128 |

FOREIGN PATENT DOCUMENTS

| CN | 1639739 A | 7/2005 |
|---|---|---|
| CN | 1915178 A | 2/2007 |
| EP | 1 219 259 B1 | 7/2003 |
| EP | 1 669 029 B1 | 8/2009 |
| JP | 07079981 A | 3/1995 |
| JP | 09024047 A | 1/1997 |

(Continued)

*Primary Examiner* — Charles V Hicks
(74) *Attorney, Agent, or Firm* — The Small Patent Law Group; Dean D. Small

(57) ABSTRACT

A method for monitoring a target in a medical display in a medical imaging apparatus includes receiving echo signals from an area of interest of a patient, extracting raw data from the received echo signals, processing the extracted raw data to display a dual mode image on the medical display, and setting a location and displaying a first marker/cursor in a first image of the dual mode image. In addition, the method further includes determining a corresponding location of the marker/cursor in a second image of the dual mode image, and displaying a second marker/cursor in the second image of the dual mode image at the corresponding location simultaneously with the displaying of the first marker/cursor in the first image.

24 Claims, 7 Drawing Sheets

(56) References Cited

FOREIGN PATENT DOCUMENTS

| | | | |
|---|---|---|---|
| JP | 09201359 | A | 8/1997 |
| JP | 11221216 | A | 8/1999 |
| JP | 2001314399 | A | 11/2001 |
| JP | 2003230559 | A | 8/2003 |
| JP | 2006122299 | A | 5/2006 |
| JP | 2006320751 | A | 11/2006 |
| JP | 2006158799 | A | 6/2008 |
| WO | WO 03/077203 | A2 | 9/2003 |

* cited by examiner

METHOD AND APPARATUS FOR OBTAINING AND/OR ANALYZING ANATOMICAL IMAGES

BACKGROUND OF THE INVENTION

This invention relates generally to ultrasound systems that image anatomical structures, and more particularly, to a method and apparatus for displaying computer-coordinated markers simultaneously on dual ultrasound images of different modes in "real time."

Ultrasound contrast imaging is used for tumor detection and characterization in some parts of the world. Microbubbles are used today as contrast agents. A physician will generally inject the contrast agent into the patient. The contrast agent is used to isolate and identify where in an organ, for example, in a liver, to perform a biopsy. Generally, there will be a biopsy bracket on the ultrasound probe. A display will provide a centerline and two guidelines giving a range within which a biopsy needle will be guided. In addition, a depth marker may also appear on the screen and the lesion may be measured.

The contrast agents are able to enter blood microcirculation for several minutes without breaking under a low mechanic index acoustic field. Contrast agents increase blood backscattering signal strength and make blood flow from small vessels visible in images in which they would be masked by a surrounding tissue echo. Because of differences in vascularity, enhancement patterns are different between normal tissue and tumors, as well as between different tumor types. The differences in enhancement patterns are used for tumor detection and characterization.

To obtain improved contrast performance, contrast imaging suppresses the tissue background to increase the contrast to tissue ratio. When a tissue background is perfectly suppressed, a target becomes difficult to see before contrast injection. A dark tissue background causes difficulty in maintaining the small lesion in an image plane due to movement from patient breath, patient motion and probe motion. For diagnosis, it is important to know the exact location of the lesion in the image and to see the contrast enhancement dynamic pattern over a period of time. Thus, a B mode image is often used as reference for monitoring the lesion position and a contrast image is displayed alongside the B mode image in real time in a dual imaging mode. The dual image mode makes it simpler to monitor the target image, but it is sometimes still difficult to know the exact position of the lesion in the contrast mode image when the lesion is small. Moreover, contrast agents do not remain in the body for an extended time. Hence, contrast examinations have a limited viewing time. In the meantime, the user (e.g., the physician) is busy storing images and clips to a hard drive in the ultrasound machine and has to concentrate on what he or she is doing during the relatively limited examination time.

Ultrasound systems may use recording systems to store a series of images. Video recorders or a digital memory are incorporated into many conventional ultrasound systems. The information stored by and played back from a digital memory is generally limited by the analysis being performed during recording. The reason for this limitation is that a conventional digital memory receives data produced after the echo signals have been processed and prepared for display. Therefore, the digital memory stores only the data resulting from a particular processing operation carried out upon the echo signals at the time the patient was examined. The processing operation is determined by the present mode of operation and parameter settings. Thus, processed data that is stored may ignore and/or eliminate certain information from the echo signals. This ignored or eliminated information cannot be recovered. For example, an abnormality recognized in a recorded image after the patient has left cannot be analyzed in greater detail unless the patient returns for a new scanning session and then only if the abnormality present during the original scanning session is again detected. Accordingly, images that are recorded while inaccurate or less than optimal parameters are set may be useless. Thus, increases in the length or number of ultrasound scanning sessions may result, thereby increasing patient exposure time, patient discomfort and procedure costs. Furthermore, studies employing contrast agents are limited in the number of different analyses that can be performed during the rapid decay of the contrast agent.

SUMMARY OF THE INVENTION

In one embodiment of the present invention, a method is provided for monitoring a target in a medical display in a medical imaging apparatus. The method includes receiving echo signals from an area of interest of a patient, extracting raw data from the received echo signals, processing the extracted raw data to display a dual mode image on the medical display, and setting a location and displaying a first marker/cursor in a first image of the dual mode image. In addition, the method further includes determining a corresponding location of the marker/cursor in a second image of the dual mode image, and displaying a second marker/cursor in the second image of the dual mode image at the corresponding location simultaneously with the displaying of the first marker/cursor in the first image.

In another embodiment of the present invention a method is provided for analyzing raw data generated by a medical imaging apparatus. The method includes processing stored raw data to generate a displayable dual mode image, determining whether or not to display markers/cursors at a saved location, and displaying the displayable dual mode image with or without the markers/cursors at the saved location, depending upon results of said determining whether or not to display markers/cursors at the saved location.

In yet another embodiment of the present invention a medical imaging apparatus is provided that includes a probe having transducers configured to transmit and receive a signal to and from a patient, a signal processor configured to process raw data resulting from signals received from the patient into a displayable image, a marker/cursor generator configured to place markers/cursors into the displayable image, and a display configured to display the displayable image. The medical imaging apparatus is configured to receive echo signals from an area of interest of a patient, extract raw data from the received echo signals, and process the extracted raw data to display a dual mode image on the medical display. The medical imaging apparatus is further configured to set a location and displaying a first marker/cursor in a first image of the dual mode image, determine a corresponding location of the marker/cursor in a second image of the dual mode image, and display a second marker/cursor in the second image of the dual mode image at the corresponding location simultaneously with the displaying of the first marker/cursor in the first image.

DETAILED DESCRIPTION OF THE INVENTION

Figure 1:
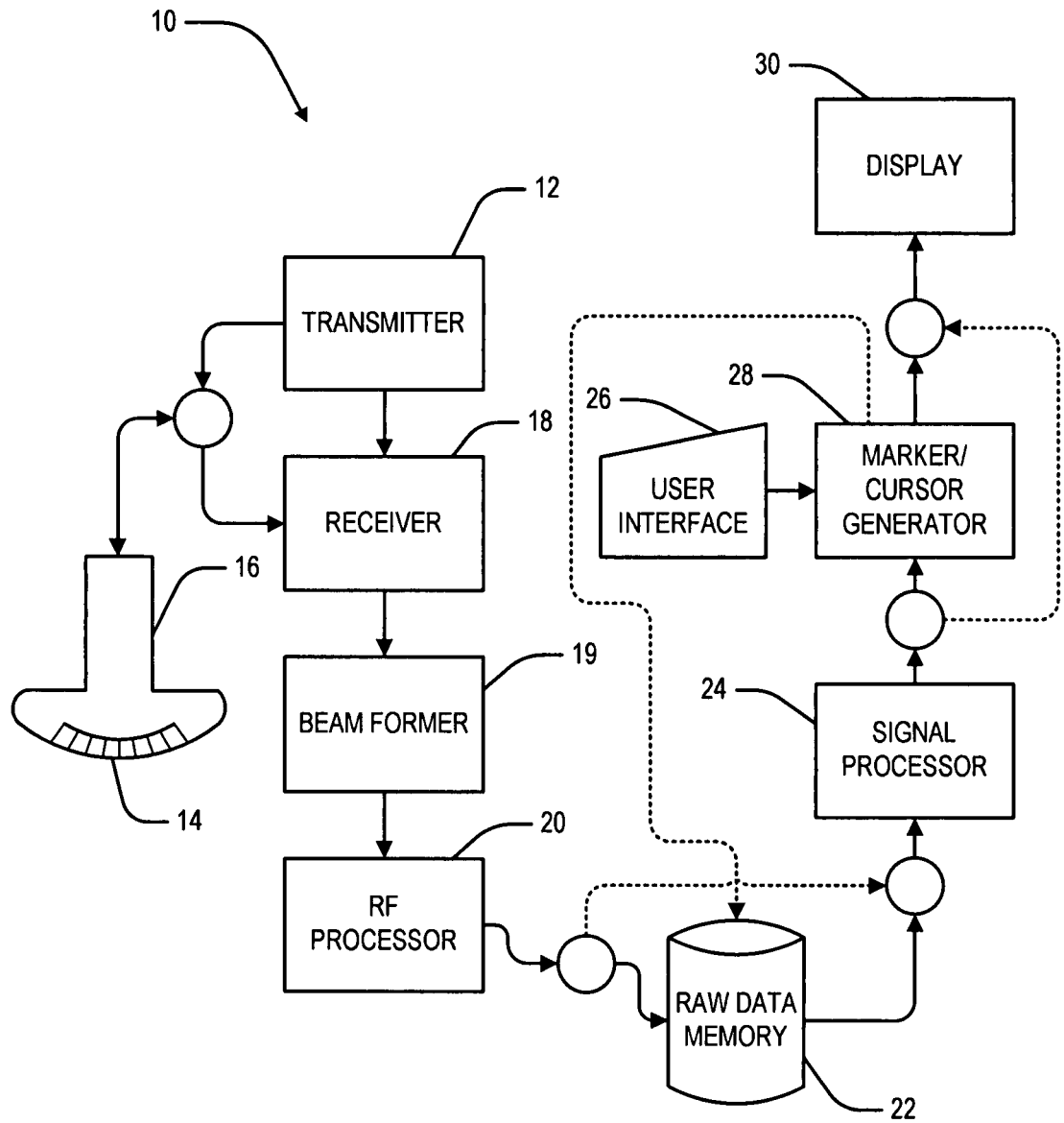
FIG. 1 is a block diagram of an ultrasound imaging system constructed in accordance with one embodiment of the present invention.

The foregoing summary, as well as the following detailed description of certain embodiments of the present invention will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional such elements not having that property.

Contrast images obtained via ultrasound have a weak tissue background. To provide a more positive identification of significant features such as, for example, tumors, some embodiments of the present invention provide a dual contrast imaging display having a B mode image side-by-side with a contrast image. The B mode image serves as a reference, for example, to help the user find the target position (e.g., the tumor position) in the contrast image. Various configurations of the present invention provide a dual marker/cursor display to synchronize the indicated target positions in the contrast image and the B mode image when an ultrasound imaging apparatus is in dual image mode.

When a lesion appears on the B mode image, a user is able to position a marker/cursor (e.g., an arrow) on the B mode image to indicate the lesion position. At the same time, the ultrasound imaging apparatus positions a marker/cursor (e.g., another arrow) at a corresponding position on the contrast image. With the help of the marker/cursor on the contrast image, a user can focus his or her attention on the contrast enhancement dynamic change of the lesion. In some embodiments of the present invention, the user is also able to activate/deactivate the dual marker/cursor display by a key or a button. The user can also select to always display the marker/cursor by default on both the B mode image and the contrast mode image.

In some embodiments of the present invention, medical image data is stored in raw form. The marker/cursor is not stored in a manner that interferes with storing an entire image. However, the marker/cursor can be stored in a separate file or a separate section of the raw image data so as to retain integrity of the raw data. (Hereinafter, either storage method shall be referred to as having the marker/cursor stored "separately from the raw data.") The stored raw data can thus be processed and viewed later with or without the marker or cursor, thereby allowing a user to view anything that might have been hidden underneath the cursor. In embodiments in which the marker/cursor is separately stored, the marker/cursor can be restored during this later processing and viewing using supplied software, firmware, and/or special purpose hardware (hereinafter referred to as "software" or "special purpose hardware" for economy of description). Also, in some embodiments, data can be transferred from the imaging apparatus to a workstation where the marker/cursor can be displayed if desired.

By separating markers/cursors that are placed on a displayed image in real time during a procedure from stored raw data, a user who finds the marker in a inconvenient location (e.g., obscuring an object of interest) can move or remove the marker, or make measurements after the examination of the patient in the case where measurements were not made during the examination.

A block diagram of one embodiment of an ultrasound system (generally indicated at 10) is shown in FIG. 1. Ultrasound system 10 includes a transmitter 12 that drives transducers 14 within a probe 16 to emit pulsed ultrasonic signals into a body. The ultrasonic signals emitted by transducers 14 are backscattered from structures in the body, like blood cells, muscular tissue, organ tissue, and/or tumors to produce echoes which return to the transducers 14. The echoes are detected by a receiver 18. The received echoes are passed through a beamformer 19 that performs beam forming and outputs an RF signal. The RF signal emitted by beamformer 19 passes through an RF processor 20. In one embodiment of the present invention, the RF signal data (raw data) may then be routed directly to a raw data memory 22 for storage. In another embodiment, RF processor 20 may include a complex demodulator (not shown) that demodulates the RF signal to form I, Q data pairs (also considered raw data) representative of the echo signals prior to storage in raw data memory 22. In some embodiments, RF processor 20 may provide both raw RF signal data or raw I, Q data pairs, or a choice of either source of raw data to store in raw data memory 22.

Ultrasound system 10 also includes a signal processor 24 to process the received echo signal data (i.e., RF signal data or I, Q data pairs) and prepare an image for display on display 30. Signal processor 24 may receive raw data either directly from RF processor 20 or from raw data memory 22 in one embodiment of the present invention. Signal processor 24 is adapted, either through software or special purpose hardware, to perform one or more processing operations from a plurality of selectable processing operations on the received echo signal data. Echo signal data may be processed and displayed in real-time during a scanning session as the echo signals are received. Additionally or alternatively, the echo signal data may be stored in raw data memory 22 during a scanning session and then, in a post-storage (off-line) operation, retrieved from raw data memory 22, processed by signal processor 24 and displayed on display 30.

Also in one embodiment of the present invention, raw data memory 22 is of sufficient capacity to store at least several seconds of echo signal data for multiple range positions along multiple scan lines. Raw data memory 22 may comprise any known data storage medium, such as magnetic storage, flash memory, RAM, and/or optical memory. Raw data memory 22 may also allow the archiving of raw data from multiple scanning sessions and/or multiple patients.

Signal processor 24 may employ any known signal processing and data manipulation techniques to provide any known ultrasound mode or analysis that has conventionally been carried out in real-time during a scanning session. In one embodiment of the present invention, signal processor 24 is configured to display a dual-mode, side-by-side image comprising a B mode image and a contrast image. Also in one embodiment, these signal processing and data manipulation techniques may be carried out in a post-storage (off-line) operation on stored raw data. Furthermore the various known parameters of signal processing and data manipulation may be selectably modified during off-line playback to optimize the displayed output.

Figure 2:
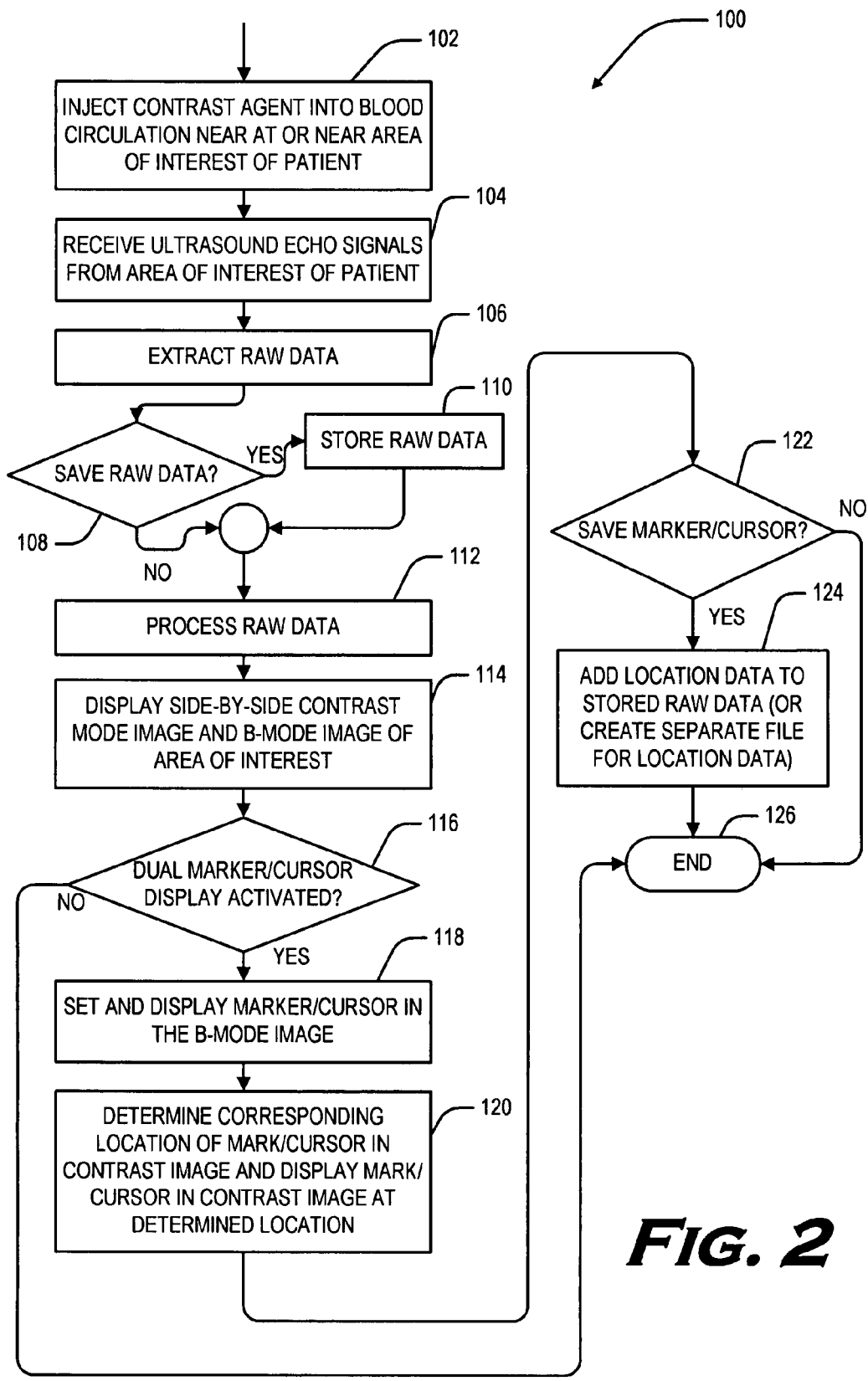
FIG. 2 illustrates a flow chart of a procedure for accumulating and storing ultrasound information in accordance with one embodiment of the present invention.

FIG. 2 illustrates a flow chart 100 of a procedure for accumulating and storing ultrasound information in one embodiment of the present invention, and that is suitable for use with ultrasound imaging apparatus 10 of FIG. 1. Starting at 102, a physician (or other individual permitted to do so) injects a contrast agent into blood circulation at or near an area of interest of a patient, such as a liver. At 104, transmitter 12, transducers 14, probe 16, receiver 18, and beam former 19 are operated to transmit and receive ultrasound echo signals (raw RF data) from an area of interest (e.g., the liver) of the patient. At 106, RF processor 20 extracts raw data, for example, in the form of raw RF data or I and Q data pairs.

Some embodiments allow the user to make a choice as to whether the raw data is stored in memory 22, as shown at 108. If the choice is to store raw data, or if an embodiment is used that always stores raw data, the raw data is stored in raw data memory 22 at 110, and the raw data is processed next (or simultaneously) at 112. Otherwise, the process continues at 112 by processing the raw data. For economy of explanation, it will be assumed hereafter that raw data is stored at 110. It will be understood that the sequence represented by 108 and 110 may occur at one or more other places in the procedure represented by flow chart 100, either as an alternative or in addition to the location in the procedure shown in flow chart 100. For example, it may be desirable in some embodiments to make a decision after step 114 (after the image is viewed) regarding whether the raw data is stored. As another example, the decision to save raw data could be made in some embodiments either before or after the decision is made to save the marker cursor location at 122.

Next, at 114, side-by-side images of the area of interest operated by signal processor 24 are displayed on display 30. In embodiments represented in FIG. 1, for example, these images can be generated either by signal processor 24, as indicated by a dashed connector, and/or by marker/cursor generator 28, without displaying a marker/cursor. Marker/cursor generator 24 may, in some embodiments, be part of signal processor 24. For purposes of economy of explanation, it will henceforth be assumed that the side-by-side images comprise a B mode image and a contrast image.

Next, at 116, if the dual marker/cursor display mode is not activated by the user by manipulating user interface 26, the procedure ends at 126. It should be understood that, rather than ending, the procedure may enter a loop or an interrupt routine, or an equivalent, to continue to display and update the display and/or allow the dual marker/cursor display mode to be activated at a later time during the current medical procedure. For example, in some embodiments of procedure 100, if the dual marker/cursor display mode is not activated at 116, the procedure may loop back to 104 to update the display. Locations can be correlated between two images because the same raw data is used to produce both of the images. Thus, pixels in 2-D images that correspond to the same physical location can be readily located. Moreover, each image has the same number of horizontal pixels and the same number of vertical pixels. Thus, because the images represent the same projection of the same physical plane, it is enough in some embodiments to indicate the same pixel pair location in both images.

If the dual marker/display mode is activated at 116, then at 118, the marker/cursor is set and displayed in the B mode image, and at 120, a corresponding location of the marker/cursor is determined and the marker/cursor is simultaneously displayed at the determined location in the contrast image. More generally, either image in the dual display mode could be used as the image on which the marker/cursor is initially set and the other as the image on which the corresponding location is determined.

Next, at 122, if the user has selected an option to save the marker/cursor location along with the raw data, the marker/cursor location is saved separately from (or in a separate section) of the raw data file corresponding to the displayed image at 124. (An image comprises information in the form of vectors representing an angle and an echo time, the latter, in combination with the speed of sound, representing a depth of the image. Each vector lasts for a certain period of time, which is mapped to the depth of the image. Thus, the saved marker/cursor location can be stored as an image ID to identify to which image the saved location relates, an angle, and an echo depth.) Otherwise, the procedure ends at 126 (or loops, as described above). The end at 126 is also reached directly from 122 if the user has not selected to save the marker/cursor location.

Figure 3:
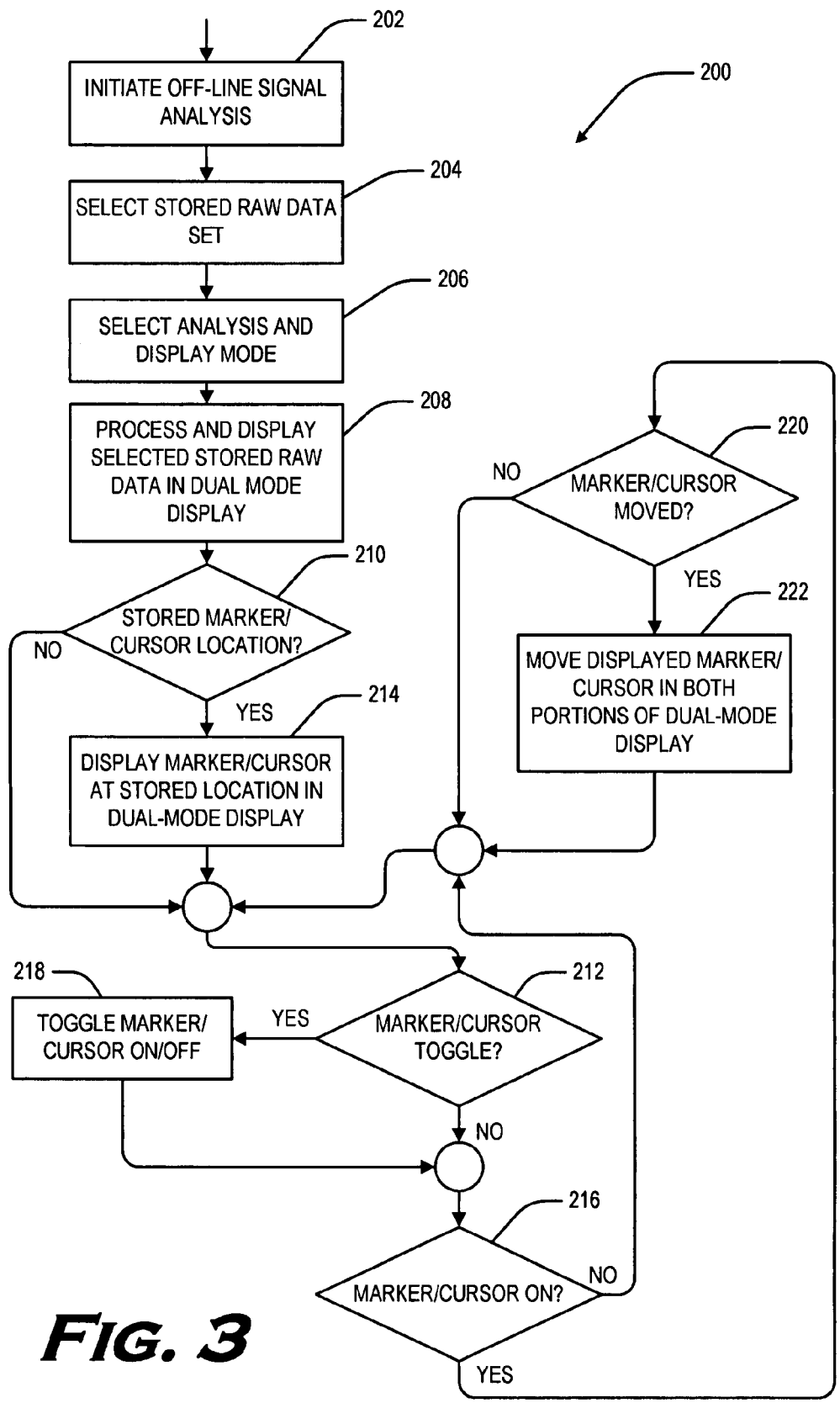
FIG. 3 illustrates a flow chart of a procedure for displaying and analyzing off-line ultrasound information in accordance with one embodiment of the present invention.

FIG. 3 illustrates a flow chart 200 of a procedure for displaying and analyzing off-line ultrasound information in one embodiment of the present invention. An off-line signal analysis is initiated at 202, either on apparatus 10 or on a computer or workstation or other suitable computer platform. To use a computer or workstation, it is presumed that stored raw data in memory 22 has either been downloaded into the memory of the computer or workstation or made available via a wired or wireless network or direct connection. Next, a stored data set is selected from the stored raw data at 204 and an analysis and display mode is selected at 206. For economy of explanation, it will be assumed that a dual mode of B mode and contrast mode is selected, so at 208, the stored data set is processed and displayed on a dual mode display.

Next, at 210, if there is a stored marker/cursor location associated with the raw data set, the marker/cursor is displayed in corresponding locations on both portions of the dual mode image at 214. Otherwise, the operation at 214 is skipped. Some embodiments of the present invention also allow a user to toggle the display of the marker/cursor, which allows the user to see undisturbed any features obscured by the marker/cursor. Thus, at 212, if the marker/cursor display has been toggled by the user, the display of the marker/cursor is toggled on or off at 218 as appropriate. In some embodiments, the user is able to specify whether the marker/cursor display is on or off, rather than toggled. In either case, at 216, the next check is to determine whether the marker/cursor display is on. If not, the procedure loops back to 212 to wait for the marker/cursor to be toggled on. Otherwise, a check is performed to determine whether, in the current display, the marker/cursor has been manually moved by the user. If not, the procedure loops back to 212. Otherwise, the marker/cursors displayed in both portions of the dual mode display are moved to the correct positions that each correspond to the movement specified by the user before the procedure loops back to 212. Thus, a user is able to display the dual mode display with or without the marker/cursor placed during a medical procedure, allowing the user to see what might have been obscured by the marker/cursor. The user is also able to display a different marker/cursor on both halves of the dual mode display, to allow measurements to be made and/or allow a different location in the region of interest to be highlighted.

Figure 4:
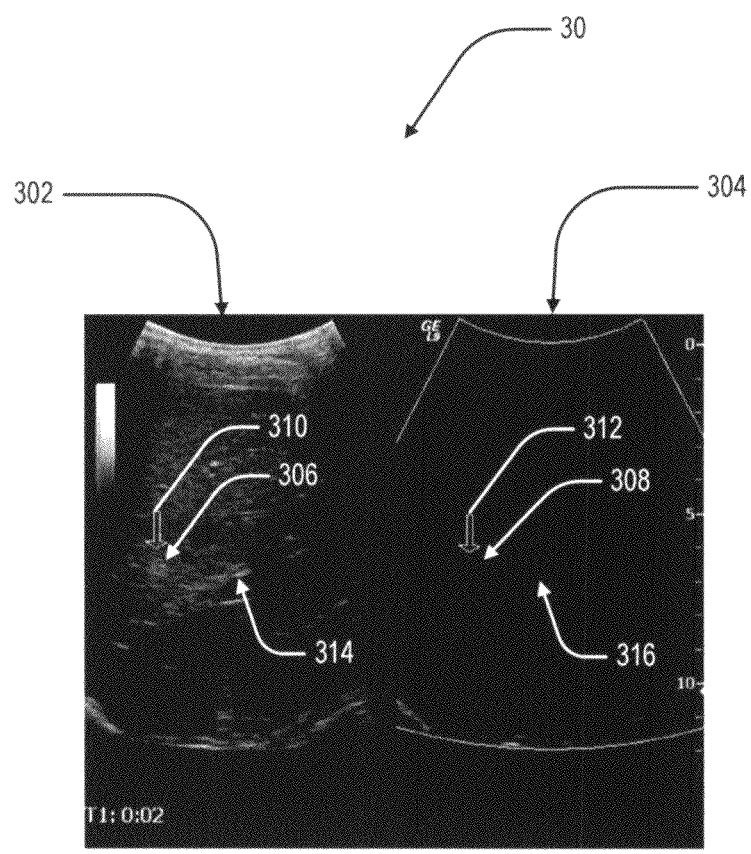
FIG. 4 illustrates an image displayed in dual contrast imaging mode by the apparatus of FIG. 1, wherein the left image is a B mode image and the right image is a contrast image.
Figure 5:
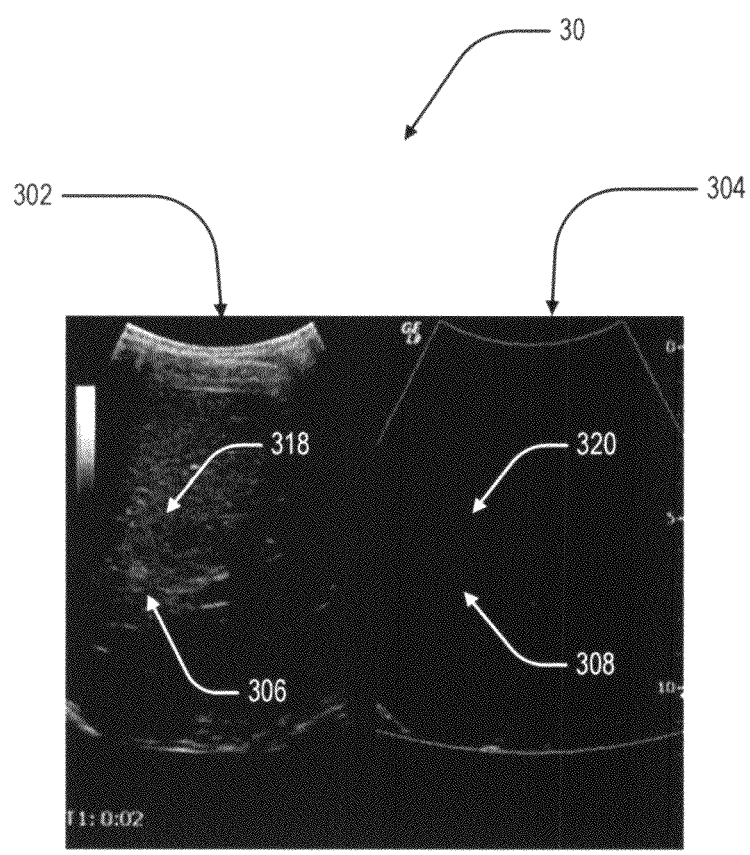
FIG. 5 illustrates an image generated by processing raw data stored by the apparatus of FIG. 1 and showing a complete image without the arrows shown in FIG. 4.
Figure 6:
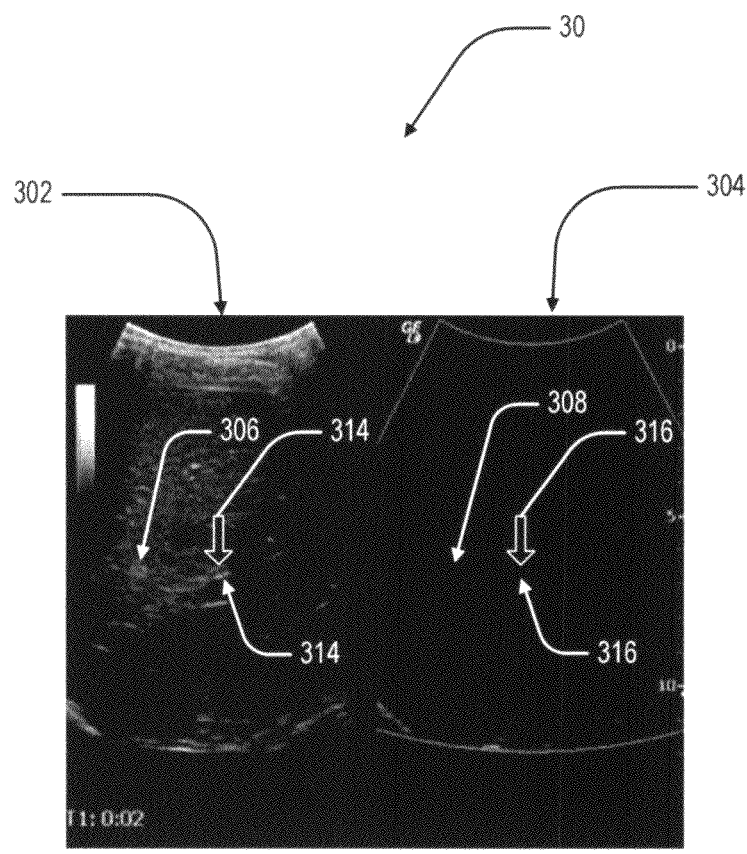
FIG. 6 illustrates an image generated by processing raw data stored by the apparatus of FIG. 1 and showing an image with an arrow displayed in corresponding locations in the B mode image and the contrast image, but moved relative to the position of the arrow in FIG. 4.

FIG. 4 illustrates a region of interest displayed on display 30 in dual contrast imaging mode by apparatus 10 of FIG. 1, wherein left image 302 is a B mode image and right image 304 is a contrast image. An arrow 310 placed by the user during an examination points to a suspected tumor 306 shown on B mode image 302. FIG. 4 could represent a display 30 during an examination or raw image data stored by apparatus 10 and processed after the examination. In the case of the display during an examination, the user may place arrow 310 on B mode image 302 and have apparatus 10 calculate and determine the corresponding location for arrow 312 on contrast image 304. In the case of raw image data stored by apparatus 10 and processed after examination, the location of arrows 310 and 312 are stored separately from the raw data (i.e., in a separate location from the raw data file or record, or in a separate section of the raw data file or record) and restored to images 302 and 304 after these images are processed from the raw data. Thus, it is possible to display a complete B mode image 302 and a complete contrast image 304 by turning the marker/cursor display off, as shown in FIG. 5, to reveal any features 318, 320 that may have been obscured by arrows 310 and 312. It is also possible to change the location of the marker/cursor to have an arrow 310 highlight a different object or structure 314 in image 302 and have apparatus 10 (or a computer or other suitable workstation) compute a location and place arrow 312 at a corresponding location to highlight the same location 316 in contrast image 304 as object or structure 314 in B mode image 302.

Figure 7:
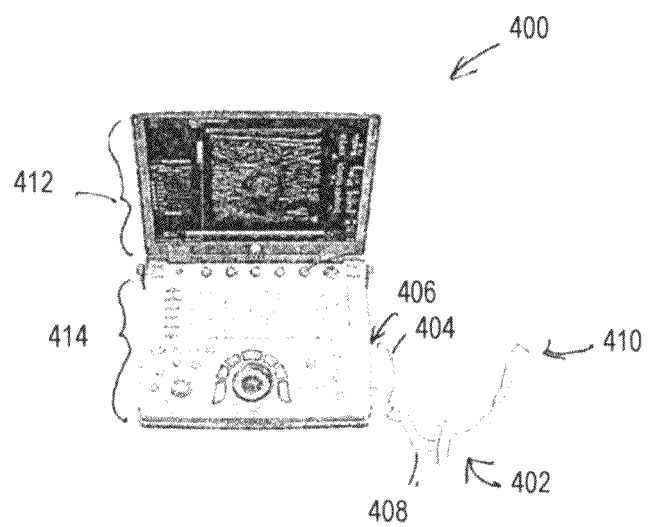
FIG. 7 illustrates a portable ultrasound system formed in accordance with an embodiment of the present invention.

FIG. 7 illustrates a miniaturized ultrasound system 400 in which various embodiments may be implemented. As used herein, "miniaturized" means that the ultrasound system is a handheld or hand-carried device or is configured to be carried in a person's hand, briefcase-sized case, or backpack. For example, ultrasound system 400 may be a hand-carried device having a size of a typical laptop computer, for instance, having dimensions of approximately 2.5 inches in depth, approximately 14 inches in width, and approximately 12 inches in height. Ultrasound system 400 may weigh about ten pounds An ultrasound probe 402 has a connector end 404 that interfaces with ultrasound system 400 through an I/O port 406 on ultrasound system 400. Probe 402 has a cable 408 that connects a connector end 404 and a scanning end 410 that is used to scan a patient. Ultrasound system 400 also has a display 412 and a user interface 414.

Figure 8:
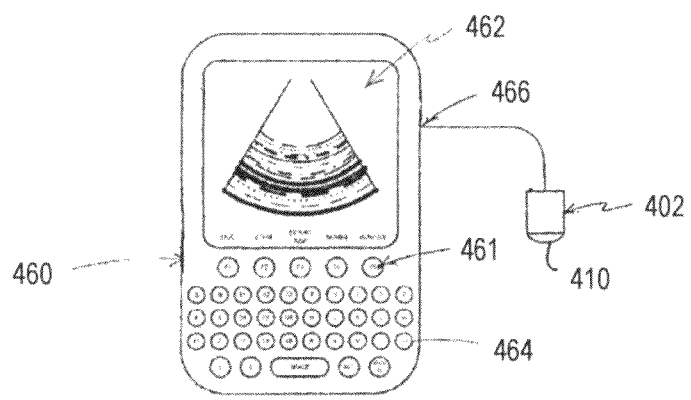
FIG. 8 illustrates an example of a pocket-sized ultrasound system formed in accordance with an embodiment of the present invention.

FIG. 8 shows an example of a pocket-sized ultrasound system 460 in which various embodiments may be implemented. By way of example, pocket-sized ultrasound system 460 may be approximately 2 inches wide, approximately 4 inches in length, and approximately 0.5 inches in depth and weigh less than 3 ounces. Pocket-sized ultrasound system 460 generally includes a display 462, a user interface 464 (e.g., a keyboard, which may include soft keys such as soft key 461) and an input/output (I/O) port 466 for connection to probe 402. It should be noted that the various embodiments may be implemented in connection with a miniaturized ultrasound system having different dimensions, weights, and power consumption. In some embodiments, the pocket-sized ultrasound system 460 may provide the same functionality as ultrasound system 400 of FIG. 7.

A technical effect of at least one embodiment of the present invention is the processing of stored raw data and the display of the processed data after the ultrasound procedure. The later processing and display of the raw data permits images to be displayed with or without a marker or cursor that may have been displayed during the ultrasound procedure, thereby allowing a user to see anything that might have been hidden underneath the marker or cursor. Also, a marker/cursor can be restored in some embodiments during this later processing and displaying by using supplied software, firmware, and/or special purpose hardware (hereinafter referred to as "software or special purpose hardware" for economy of description). Also, in some embodiments, a technical effect is the communication of raw data from the imaging apparatus to a workstation by the imaging apparatus. In these embodiments, the marker/cursor can be displayed or not, as the user chooses. Furthermore, a user who finds the marker in an inconvenient location (e.g., obscuring an object of interest) can move or remove the marker, or make measurements after the examination of the patient in case such measurements were not made during the examination.

Also, it will be appreciated that, in some embodiments of the present invention, the real time dual mode display of an imaging apparatus can be used by a user to place a marker/cursor on one side of the dual mode display (e.g., the B mode image) to indicate a lesion position. At the same time, the imaging apparatus can place a marker/cursor at the same position on the other side of the dual mode display (e.g., a contrast image). With the help of the marker/cursor on the other side of the dual mode display, it can be much easier for a user to focus his or her attention (e.g., on the contrast enhancement dynamic change of a lesion).

While the invention has been described in terms of various specific embodiments, those skilled in the art will recognize that the invention can be practiced with modification within the spirit and scope of the claims.

What is claimed is:

1. A method for monitoring a target in a medical display in a medical imaging apparatus, said method comprising:

receiving signals from the medical imaging apparatus corresponding to an area of interest of a patient;

extracting raw data from the received signals;

processing the extracted raw data to display a dual mode image on a medical display of the medical imaging apparatus;

setting a location for an object of interest during a scanning session as the signals are received and displaying a first marker/cursor in a first image of the dual mode image based on the setting of the location, the location set by a user during the scanning session;

determining a corresponding location of the marker/cursor in a second image of the dual mode image;

displaying a second marker/cursor in the second image of the dual mode image at the corresponding location simultaneously with the displaying of the first marker/cursor in the first image; and moving the location of the first marker/cursor or second marker/cursor away from the displayed object of interest to another display location after the scanning session.

2. The method of claim 1 wherein the transducers are ultrasound transducers.

3. The method of claim 1 further comprising selecting whether or not a marker/cursor is to be displayed, and conditioning at least said displaying of the first marker/cursor and said displaying of the second marker/cursor upon the selection of whether or not a marker/cursor is to be displayed.

4. The method of claim 1 further comprising storing the extracted raw data in a raw data memory.

5. The method of claim 1 further comprising at least one of storing the marker/cursor location to the stored raw data and storing the marker/cursor location to a separate file.

6. The method of claim 1 further comprising selecting whether or not a marker/cursor is to be displayed in accordance with a preset, and conditioning at least said displaying of the first marker/cursor and said displaying of the second marker/cursor upon the selection of whether or not a marker/cursor is to be displayed.

7. The method of claim 1 wherein the first image is a B mode image and the second image is a contrast image.

8. A method for analyzing raw data generated by an ultrasound imaging apparatus, said method comprising:
processing stored raw data acquired from the ultrasound imaging apparatus to generate a displayable dual mode image;
determining whether or not to display markers/cursors at a saved location after a scanning session, and positioned during acquisition of the raw data, wherein a received user input associates an obscured object of interest with one of the markers/cursors; and
displaying the displayable dual mode image with or without the markers/cursors at the saved location, depending upon results of said determining whether or not to display markers/cursors at the saved location.

9. The method of claim 8 performed using the ultrasound imaging apparatus.

10. The method of claim 8 performed on a computer or a workstation, and said method further comprising making contents of the raw data memory available for processing that uses the computer or workstation.

11. The method of claim 8 wherein the dual mode display comprises a side-by-side B mode display and a contrast display.

12. The method of claim 8 further comprising selectively enabling and disabling display of markers/cursors during said analyzing.

13. The method of claim 8 further comprising moving a marker/cursor to corresponding locations in each portion of the dual mode display during said analyzing.

14. The method of claim 13 further comprising selectively enabling and disabling display of markers/cursors during said analyzing.

15. A medical imaging apparatus comprising:
a probe having transducers configured to transmit and receive a signal to and from a patient, a signal processor configured to process raw data resulting from signals received from the patient into a displayable image, a marker/cursor generator configured to place markers/cursors into the displayable image, and a display configured to display the displayable image,
said medical imaging apparatus configured to:
receive echo signals from an area of interest of a patient;
extract raw data from the received echo signals;
process the extracted raw data to display a dual mode image on the medical display;
set a location during a scanning session as the echo signals are received and display a first marker/cursor in a first image of the dual mode image, wherein the location is set by a user during the scanning session;
determine a corresponding location of the marker/cursor in a second image of the dual mode image;
display a second marker/cursor in the second image of the dual mode image at the corresponding location simultaneously with the displaying of the first marker/cursor in the first image, wherein the location identifies an object of interest; and
determine, after the scanning session, whether to display the first marker/cursor or second marker/cursor, or move the first or second marker/cursor to a different display location, based on a received user input indicating whether the first marker/cursor or second marker/cursor obscures the object of interest.

16. The apparatus of claim 15 wherein the transducers are ultrasound transducers.

17. The apparatus of claim 15 further configured to accept a user's selection of whether or not a marker/cursor is to be displayed, and to condition at least the display of the first marker/cursor and the display of the second marker/cursor upon the user's selection of whether or not a marker/cursor is to be displayed.

18. The apparatus of claim 15 further having a raw data memory, and said apparatus configured to store the extracted raw data in the raw data memory.

19. The apparatus of claim 15 further configured to at least one of store the marker/cursor location to the stored raw data and store the marker/cursor location to a separate file.

20. The apparatus of claim 15 further configured to select whether or not a marker/cursor is to be displayed in accordance with a preset, and to condition at least the display of the first marker/cursor and the display of the second marker/cursor upon the selection of whether or not a marker/cursor is to be displayed.

21. The method of claim 1 wherein moving the location of the first marker/cursor or second marker/cursor away from the displayed object of interest to another display location comprises moving the marker from a location obscuring an object of interest to a location not obscuring the object of interest.

22. The method of claim 8 wherein the markers/cursors are placed on an image displayed in real time during a procedure and stored along with the raw data.

23. The method of claim 8 further comprising storing the location of the markers/cursors as location data separate from the raw data, the stored location data associated with an image and including angle and echo depth information corresponding to and identifying the image for subsequent retrieval.

24. The method of claim 23 further comprising subsequently identifying the location of the markers/cursors offline by accessing and using the stored location data to display the markers/cursors at pixel locations of an image based on the stored location data such that the markers/cursors are restored to the location set by the user during the scanning session, and further comprising receiving a user input moving the location of at least one of the markers/cursors to a different display position and displaying the different display location, and storing the different display position separate from the raw data as location data allowing subsequent accessing of the location data and display of the markers/cursors in the location or the different display location.

* * * * *